(12) United States Patent
Schmitz et al.

(10) Patent No.: US 8,257,729 B2
(45) Date of Patent: Sep. 4, 2012

(54) IMPLANTS WITH MEMBRANE DIFFUSION-CONTROLLED RELEASE OF ACTIVE INGREDIENT

(75) Inventors: Klaus-Peter Schmitz, Warnemuende (DE); Detlef Behrend, Rostock (DE); Katrin Sternberg, Rostock (DE); Niels Grabow, Rostock (DE); Claus Harder, Uttenreuth (DE); Bjoern Klocke, Zurich (CH); Heyo K. Kroemer, Neuenkirchen (DE); Werner Weitschies, Neuenkirchen (DE)

(73) Assignees: Biotronik VI Patent AG, Baar (CH); Universitaet Rostock, Rostock (DE); Universitaet Greifswald, Greifswald (DE)

( * ) Notice: Subject to any disclaimer, the term of this patent is extended or adjusted under 35 U.S.C. 154(b) by 775 days.

(21) Appl. No.: 12/331,567

(22) Filed: Dec. 10, 2008

(65) Prior Publication Data
US 2009/0148496 A1 Jun. 11, 2009

(30) Foreign Application Priority Data
Dec. 10, 2007 (DE) .......................... 10 2007 059 755

(51) Int. Cl.
A61F 13/00 (2006.01)
A61F 2/00 (2006.01)
A61F 2/06 (2006.01)
(52) U.S. Cl. ....... 424/424; 424/422; 623/1.42; 623/1.46
(58) Field of Classification Search .................. None
See application file for complete search history.

(56) References Cited

U.S. PATENT DOCUMENTS

| 5,968,083 | A | 10/1999 | Ciciarelli et al. |
| 6,197,047 | B1 | 3/2001 | Kranz |
| 6,753,071 | B1 * | 6/2004 | Pacetti .......................... 428/212 |
| 6,896,695 | B2 | 5/2005 | Mueller et al. |
| 2004/0034409 | A1 * | 2/2004 | Heublein et al. ............. 623/1.46 |
| 2005/0025799 | A1 * | 2/2005 | Hossainy et al. ............. 424/423 |
| 2006/0241742 | A1 | 10/2006 | Harder et al. |

FOREIGN PATENT DOCUMENTS

| DE | 29724864 U1 | 11/2004 |
| DE | 102005021622 A1 | 11/2006 |
| DE | 102006038239 A1 | 2/2008 |
| DE | 60316579 T2 | 7/2008 |
| EP | 0884985 | 12/1998 |
| EP | 1430854 A1 | 6/2004 |
| WO | 03000156 A1 | 1/2003 |
| WO | 2004006885 A2 | 1/2004 |
| WO | 2005061024 A1 | 7/2005 |
| WO | 2006118937 A2 | 11/2006 |

OTHER PUBLICATIONS

Search Report for German Patent Application No. 10 2007 059 755.1; Aug. 25, 2008.

* cited by examiner

*Primary Examiner* — Carlos Azpuru
*Assistant Examiner* — Casey Hagopian
(74) *Attorney, Agent, or Firm* — Biotech Beach Law Group PC

(57) ABSTRACT

An implant for implantation in a human or animal body having a structure comprising a) an implant base body; b) a primer layer which is partially or completely applied to the surface of the implant; c) an active ingredient layer consisting of one, two, three or more active ingredients applied entirely or partially to the surface of the primer layer; and d) a diffusion-controlling layer which is applied partially or entirely to the active ingredient layer, and optionally to the primer layer, wherein diffusion of the active ingredients of the active ingredient layer is controlled. Also disclosed is a manufacturing method for an implant.

15 Claims, 1 Drawing Sheet

IMPLANTS WITH MEMBRANE DIFFUSION-CONTROLLED RELEASE OF ACTIVE INGREDIENT

PRIORITY CLAIM

This patent application claims priority to German Patent Application No. 10 2007 059 755.1, filed Dec. 10, 2007, the disclosure of which is incorporated herein by reference in its entirety.

FIELD

The present disclosure relates to a medical implant containing a controllably releasable composition for implantation in a human or animal body and a method for manufacturing such an implant.

BACKGROUND

Implants are substances or parts that are introduced into the human or animal body to fulfill certain substitute functions for a limited period of time or for life. In contrast with transplants, implants are made of an artificial material (alloplasty). A distinction is often made between medicinal, plastic and functional implants.

Medicinal implants have the task of supporting or replacing body functions. Depending on function, the medicinal implants are also referred to as implantable prostheses. Examples of medicinal implants include, for example, heart pacemakers, brain pacemakers for Parkinson's disease, heart implants, cochlear implants, implants in dental medicine, stents and implants that serve to form a depot of a pharmaceutical substance and various forms of joint replacements.

Plastic implants are used in plastic surgery, e.g., to replace body parts that have been destroyed or to change existing body parts.

Functional implants are used to monitor human or animal functions by implanting radiofrequency identification (RFID) chips subcutaneously.

From the variety of existing types of implants, it is possible to discern that implants and their use in medicine have gained great importance.

Some considerable adverse effects are to be expected with traditional treatment principles, e.g., in systemic administration of one or more active ingredients, for example, in tumor therapy, so that local controlled release of active ingredients at the target site or in the vicinity thereof has been gaining increasing relevance (local drug delivery concept (LDD) concept). To be able to perform this local administration of active ingredients, implant base bodies, in particular, are coated with active ingredients which are implanted either at the target site or in its vicinity in a human or animal body and thereby release active ingredients. This method, which has been established clinically, is used millions of times worldwide each year and it is anticipated that demand for new materials and new forms of administration will grow in view of the demographic shift within the age pyramid.

In the orthopedic field, implant-associated infections and thromboembolic complications are known to occur in conjunction with endoprosthetic implants. Research has, therefore, been conducted with implants coated with active ingredients in this field, in particular, antibiotic-coated implants.

In the field of cardiovascular diseases, minimally invasive forms of treatment offer an increasingly well-established method of treatment for dilatation and stabilization of stenosed coronary vessels through percutaneous transluminal coronary angioplasty (PCTA) and stent implantation. To achieve a further reduction in the incidence of late complications, in particular, in repeat narrowing of a vessel after PCTA (in-stent restenosis (ISR)), especially in high-risk patients, current research has pursued the goal of local administration of the active ingredients by means of a medication-coated stent (drug eluting stents (DES)).

The incidence of complications occurring with the conventional methods of the LDD concept so far, which is not to be underestimated, is due to partial bolus-like release of the active ingredients at the site of administration which can result in a local overdose of the active ingredients.

Known drug eluting stents usually comprise an active ingredient which is present in dispersed form in a polymer coating and/or within a layer of a polymer coating such that the polymer coating containing the active ingredient is applied to the base body of the stent.

Such a polymer layer with the active ingredient incorporated into it usually has a layer thickness of 10 μm to 20 μm so that when the stent braces are coated on all sides the wall thickness of the stent is approximately doubled. Various investigations, in particular, the ISAR-STEREO study, have now found that the risk of restenosis after PCTA also increases with the increase in wall thickness of the stent.

Furthermore, with such a polymer coating, it may be difficult to achieve adequate pharmacokinetics of the active ingredients at the target site in the human or animal body.

International Patent Publication No. WO 2006/118937 discloses stents which are designed so that the release of active ingredients embedded in polymer matrices is controlled.

U.S. Pat. No. 6,753,071 discloses implantable medical products, in particular, stents, which have a coating that reduces the rate of release of the active ingredient incorporated into a polymer layer.

SUMMARY

The present disclosure describes several exemplary embodiments of the present invention.

One aspect of the present disclosure provides an implant having a structure for implantation in a human or animal body, the implant comprising a) an implant base body; b) a primer layer applied at least partially to the surface of the implant; c) an active ingredient layer consisting of one or more active ingredients applied to at least a portion of the surface of the primer layer; and d) a diffusion-controlling layer applied to at least a portion of the active ingredient layer wherein diffusion of the active ingredients of the active ingredient layer is controlled.

Another aspect of the present disclosure provides a method for manufacturing an implant, the method comprising a) providing an implant having a structure for implantation in a human or animal body, the implant comprising (i) an implant base body; (ii) a preparation for the primer layer comprising one or more primer materials; (iii) a preparation for the active ingredient layer comprising one or more active ingredients; and (iv) a preparation for the diffusion-controlling layer comprising one or more polymers and one or more solvents; b) coating at least a portion of the implant base body with the preparation for the primer layer; c) coating at least a portion of the at least partially coated implant base body from step b) with the preparation for the active ingredient layer; and d) coating at least a portion of the at least partially coated implant base body from c) with the preparation for the diffusion-controlling layer.

A further aspect of the present disclosure provides an implant for implantation in a human or animal body that will allow improved physiological and/or physicochemical properties, in particular, improved controlled release of active ingredient.

In the present disclosure, a smaller layer thickness is attained for the active ingredient layer and thus a smaller total layer thickness, preferably a wall thickness for an inventive stent, is realized with the same or better adhesion properties. Furthermore, the diffusion-controlling layer d) allows controlled release of active ingredient, so that local overdosing is prevented, in particular, bolus-like release of the active ingredient.

Because of the special primer materials used, the coating may be applied to virtually all implant surfaces. This also improves the medical care because of the improved LDD therapy.

Accordingly, an implant based on the present disclosure allows optimized release, because it is controlled, of one or more active ingredients through the diffusion-controlling layer with simultaneous optimization of the treatment or prevention, in particular, in the case of stents, by minimizing the risk of restenosis due to the reduction in the wall thickness of the stent.

Implants and/or implant base bodies according to the present disclosure may include all medical implants and/or implant base bodies and are selected, for example, from the group consisting of heart pacemakers; brain pacemakers; heart implants; pacemaker electrodes; defibrillation electrodes; cochlear implants; implants for dental medicine; depot implants that serve to form a depot of an active ingredient; biodegradable or permanent coronary or peripheral stents; biodegradable or permanent stents for other internal cavities, preferably the esophagus, the bile duct, the urethra, the prostate or the trachea; and local drug delivery (LDD) implants, which are preferably implanted endovascularly in the blood vessel or other internal cavities. Preferred stents are either permanent or biodegradable coronary stents (e.g., coronary stent) and, of these, biodegradable metal stents are especially preferred.

In addition to these requirements, the original mechanical functions of a coronary stent should be retained, e.g., dilatability, low recoil, stability over a desired period of time (in the case of degradable stents comprising magnesium and its alloys, for example) and flexibility.

BRIEF DESCRIPTION OF THE DRAWINGS

Various aspects of the present disclosure are described hereinbelow with reference to the accompanying figures.

DETAILED DESCRIPTION

Figure 1:
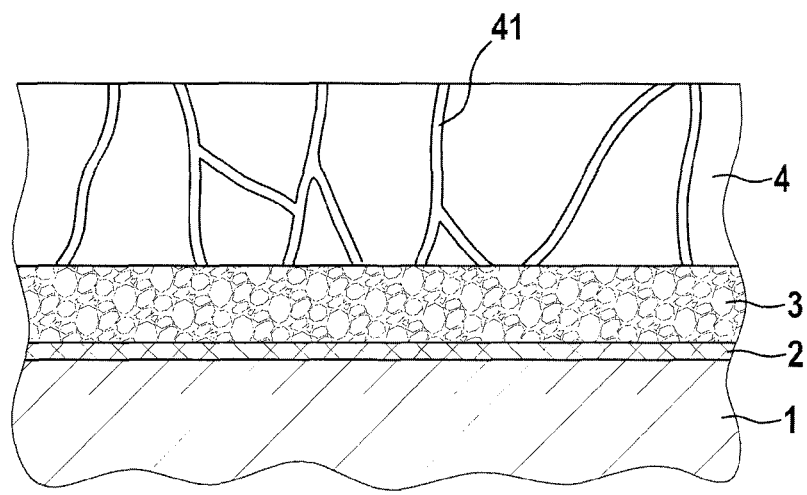
FIG. 1 shows a detail of a cross section of a web of a stent coated according to the present disclosure.

Implant materials to be used according to the present disclosure and exemplary embodiments thereof are described below.

Biodegradable Implant Base Body in Particular, Biodegradable Stent

For purposes of the present disclosure, "biodegradable implant base body," in particular, "biodegradable stent," means that the base body is degraded in a physiological environment, in particular, in the vascular system of a human or animal body, i.e., is degraded so that the stent loses its integrity. Biodegradable implant base bodies preferably degrade only when the function of the implant is no longer physiologically appropriate and/or necessary. In the case of biodegradable stents, this means that the stent is preferably degraded or loses its integrity only when the traumatized tissue of the blood vessel has healed and the stent need no longer remain in the vascular lumen.

Metallic Base Bodies

The biodegradable material is preferably a metallic material which is a biocorrodable alloy. The main component of the alloy is selected from the group consisting of magnesium, iron, zinc and tungsten. A magnesium alloy, in particular, is preferred for a degradable metallic material.

The composition of the alloy comprising one or more of the following elements, magnesium, iron, zinc and tungsten, in particular, is to be selected so that the alloy is biocorrodable. For purposes of the present disclosure, biocorrodible refers to alloys in which degradation takes place in the physiological environment, ultimately resulting in the entire stent or the part of the stent formed from the material losing its mechanical integrity. For purposes of the present disclosure, an alloy is a metallic structure whose main component is magnesium, iron, zinc or tungsten. The main component is the alloy component whose amount by weight in the alloy is the greatest. The amount of the main component is preferably more than 50 wt %, more preferably more than 70 wt %. A magnesium alloy is preferred.

If the material is a magnesium alloy, the alloy preferably contains yttrium and other rare earth metals because such an alloy is preferred because of its physicochemical properties and its high biocompatibility, in particular, its degradation products.

Magnesium alloys of the WE series, in particular, WE43, and magnesium alloys of the following composition are especially preferred: 5.5-9.9 wt % rare earth metals, including 0.0-5.5 wt % yttrium and remainder <1 wt %, which may contain zirconium and/or silicon, such that magnesium accounts for the remaining amount of alloy up to a total of 100 wt %. These magnesium alloys have already confirmed their special suitability in experiments and in initial clinical trials, i.e., the magnesium alloys have a high biocompatibility, favorable processing properties, good mechanical characteristics and an adequate corrosion behavior for the intended purpose. For purposes of the present disclosure, the collective term "rare earth metals" includes scandium (21), yttrium (39), lanthanum (57) and the 14 elements that follow lanthanum (57), namely, cerium (58), neodymium (60), promethium (61), samarium (62), europium (63), gadolinium (64), terbium (65), dysprosium (66), holmium (67), erbium (68), thulium (69), ytterbium (70) and lutetium (71).

Polymer Base Body

Implant base bodies, in particular, stent base bodies, may also consist of a biodegradable polymer material, preferably polydioxanone, polyglycolide, polycaprolactone; polyhydroxyvaleric acid, polyhydroxybutyric acid, polylactides, preferably poly(L-lactide), poly(D-lactide), poly(D,L-lactide) and blends as well as copolymers and preferably poly(L-lactide-co-glycolide), poly(D,L-lactide-co-glycolide), poly(L-lactide-co-D,L-lactide), poly(L-lactide-co-trimethylene carbonate) and tri-block copolymers; polysaccharides, preferably chitosan, levan, hyaluronic acid, heparin, dextran and cellulose.

Permanent Implant Base Bodies, Preferably Permanent Stent Base Bodies

In contrast with the biodegradable base body, the "permanent implant base body," preferably the "permanent stent base body," is essentially not degraded in a physiological environment in the human or animal body, so the permanent implant base body retains its integrity.

In another exemplary embodiment, the base body of a permanent implant, in particular, a permanent stent, consists of a memory material, one or more materials selected from the group consisting of nickel-titanium alloys and nickel-copper-aluminum alloys, preferably Nitinol.

In another exemplary embodiment, the base body of a permanent implant, in particular, a stent, is made of stainless steel, preferably a Cr—Ni—Fe steel, here preferably the alloy 316L, or a Co—Cr steel.

Furthermore, the base body of the stent may be made at least partially of plastic, preferably polyetherurethane and/or a ceramic.

For purposes of the present disclosure, if endovascularly implantable stents are used as implantable base bodies, then all conventional stent geometries may be used. Stent geometries, such as those described, in particular, in U.S. Pat. No. 6,896,695; U.S. Patent Publication No. 2006/241742; U.S. Pat. No. 5,968,083; European Patent Application No. 1 430 854; U.S. Pat. No. 6,197,047; and European Patent Application No. 0 884 985, are preferred.

The exemplary embodiments of the implant base body may be combined with one another in all conceivable variants but also with the exemplary embodiments that are also disclosed herein.

For purposes of the present disclosure, one or more conventional materials may be selected for the primer layer such that the materials usually do not enter into a significant interaction or have no reaction at all with the active ingredients of the active ingredient layer. If the diffusion-controlling layer is a degradable layer, the primer layer prevents or reduces the release of heavy metal ions out of the implant base body after implantation of the implant and during or after degradation of the diffusion-controlling layer. Furthermore, the primer layer is preferably selected so that it can form an adhesive bond with the diffusion-controlling layer.

In another exemplary embodiment of the present disclosure, the primer layer is selected from one or more materials from the group consisting of silicon carbide (SiC), diamond-like carbon (DLC), pyrolytic carbon (pyC), parylene, glycocalix and hydroxyapatite or combinations of one or more of the foregoing. Parylenes (poly-para-xylenes) are preferably selected from the group consisting of parylene N, parylene C and parylene D (GALXYL®). The primer layer preferably comprises one or more materials selected from the group consisting of silicon carbide (SiC), diamond-like carbon (DLC), pyrolytic carbon (pyC) and parylene.

The primer layer is usually entirely or partially applied to the surface of the implant base body. The primer layer usually mediates the adhesion of the active ingredients of the active ingredient layer to the implant base body. For the case when the active ingredient layer is not applied to the entire surface of the primer layer according to the present disclosure, the primer layer preferably also mediates the adhesion of the diffusion-controlling layer to the implant base body.

The exemplary embodiments of the primer layer that may be used can be combined in all conceivable variants but also with the other exemplary embodiments disclosed herein.

For purposes of the present disclosure, the polymers, in particular, also the molecular weight of the polymers and the layer thickness of the diffusion-controlling layer, are usually selected so that they prevent a bolus-type release of active ingredients and allow a suitable release of active ingredients. In addition, the substances may be incorporated into the diffusion-controlling layer, these substances being dissolved out of the diffusion-controlling layer by the tissue fluid after implantation thus forming diffusion channels through which suitable release of the active ingredient is further made possible.

In this sense, layer thicknesses of the diffusion-controlling layer in the range of 5 μm to 20 μm, preferably in the range of 5 μm to 10 μm, are generally used for the implants.

These layer thicknesses are based on the need for preferably using hydrophobic polymers for the diffusion-controlling layer, polymers that allow the required introduction of water into the layer within the desired periods of time in the stated layer thickness range for the active ingredients.

The molecular weight of the polymers of the diffusion-controlling layer is usually in the range of 100,000 g/mol to 1,000,000 g/mol, preferably in the range of 300,000 g/mol to 700,000 g/mol, more preferably in the range of 400,000 g/mol to 650,000 g/mol.

If one or more substances are incorporated into the diffusion-controlling layer and are then dissolved out of the diffusion-controlling layer after implantation, then these substances are usually substances that are dissolved out of the diffusion-controlling layer under physiological conditions and thereby form diffusion channels through the diffusion-controlling layer. Such substances are preferably selected from the group consisting of antiphlogistics (e.g., dexamethasone, methylprednisolone), cytostatics (e.g., paclitaxel, colchicine, actinomycin D, methotrexate) and immunosuppressants (e.g., sirolimus, pimecrolimus, biolimus A9, tacrolimus, cyclosporin A, mycophenolic acid), platelet aggregation inhibitors (e.g., abciximab, iloprost), substances to promote wound healing (e.g., 17β-estradiol, genistein) and extracellular matrix modulators/migration inhibitors (e.g., tretinoin, MMP-inhibitors).

In an exemplary embodiment of the present disclosure, the diffusion-controlling layer is selected from one or more polymers comprising materials selected from the group consisting of polyesters, preferably polydioxanone, polyglycolide, polycaprolactone, polyhydroxyvaleric acid, polyhydroxybutyric acids, polylactides and copolymers; polyurethanes; silicones; polyorganophosphazenes; polymethacrylates; polystyrene block copolymers; polyethylene-co-vinyl acetate; polyethylene terephthalate and blends or copolymers thereof; and phosphorylcholine polymers and polysaccharides, preferably chitosan, hyaluronic acid, heparin, dextran and cellulose.

One or more polymers of the diffusion-controlling layer according to the present disclosure are preferably selected from the group consisting of biodegradable polyesters (polyhydroxyalkanoic acids); polydioxanone; polyglycolide; polycaprolactone; polyhydroxyvaleric acid; polyhydroxybutyric acids; polylactides, preferably poly(L-lactide), poly(D-lactide), poly(D,L-lactide) and blends and copolymers thereof, such as preferably poly(L-lactide-co-glycolide), poly(D,L-lactide-co-glycolide), poly(L-lactide-co-D,L-lactide), or poly-(L-lactide-co-trimethylene carbonate).

For purposes of the present disclosure, the diffusion-controlling layer partially or completely surrounds the implant (form-fitting connection). When the active ingredient layer according to the present disclosure is partially applied to the primer layer, preferably in the form of islands of active ingredient, the diffusion-controlling layer is preferably also in contact with the primer layer. Through this contact between the primer layer and the diffusion-controlling layer there is additional adhesion which can reduce the risk of stripping the diffusion-controlling layer and possibly also the active ingredient layer from the implant due to the frictional forces during implantation.

Polymers of the diffusion-controlling layer which preferably adhere well to the primer materials are preferably selected from the group consisting of biodegradable polyesters (polyhydroxyalkanoic acids); polydioxanone; polyglycolide; polycaprolactone; polyhydroxyvaleric acid; polyhydroxybutyric acid; polylactides, preferably poly(L-lactide), poly(D-lactide), poly(D,L-lactide) and blends and copolymers thereof, preferably poly(L-lactide-co-glycolide), poly (D,L-lactide-co-glycolide), poly(L-lactide-co-D,L-lactide) and poly-(L-lactide-co-trimethylene carbonate), which form an especially good adhesion to the primer materials due to the development of van der Waals' forces.

The diffusion-controlling layer usually has a layer thickness in the range of 5 µm to 20 µm, preferably in the range of 5 µm to 10 µm.

The exemplary embodiments of the diffusion-controlling layer that may be used according to the present disclosure may be combined with one another in all conceivable variants but also with the other exemplary embodiments disclosed herein.

For purposes of the present disclosure, an active ingredient is a substance which enters into a biological reaction in the human or animal body. In this sense, an active ingredient may also be synonymous with medication and/or a pharmaceutical drug.

For purposes of the present disclosure, the term "active ingredient layer" refers to a complete coating of the primer layer on the implant base body as well as a partial coating of the primer layer, e.g., in the form of islands of active ingredient, which are understood to comprise one or more active ingredients and which may be the same or different independently of one another.

Preferred active ingredients for an implant according to the present disclosure are preferably selected from a group consisting of antiphlogistics, preferably dexamethasone, methylprednisolone and diclofenac; cytostatics, preferably paclitaxel, colchicine, actinomycin D and methotrexate; immunosuppressants, preferably limus compounds, more preferably sirolimus (rapamycin), zotarolimus (ABT-578), tacrolimus (FK-506), everolimus, biolimus, in particular, biolimus A9 and pimecrolimus, cyclosporin A and mycophenolic acid; platelet aggregation inhibitors, preferably abciximab and iloprost; statins, preferably simvastatin, mevastatin, atorvastatin, lovastatin, pitavastatin and fluvastatin; and estrogens, preferably 17β-estradiol, daidzein and genistein; lipid regulators, preferably fibrates; Immuno-suppressants; vasodilators, preferably sartans; calcium channel blockers; calcineurin inhibitors, preferably tacrolimus; anti-inflammatory drugs, preferably imidazoles; antiallergics; oligonucleotides, preferably decoy oligodeoxynucleotide (dODN); endothelium-forming agents, preferably fibrin; steroids; proteins; peptides; proliferation inhibitors; analgesics and antirheumatics. Paclitaxel and limus compounds are especially preferred according to the present disclosure. More especially preferred are sirolimus (rapamycin), zotarolimus (ABT-578), tacrolimus (FK-506), everolimus, biolimus, in particular, biolimus A9 and pimecrolimus, most especially preferably rapamycin (sirolimus).

Table 1 gives a list of active ingredients preferred for use according to the present disclosure.

TABLE 1

Summary of preferred active ingredients

| Anti-proliferative and/or anti-inflammatory substances | Anti-thrombogenic substances | Migration inhibitors/ECM modulators | Wound healing/endothelialization-promoting agents |
| --- | --- | --- | --- |
| Sirolimus | Hirudine | Probucol | 17β-Estradiol |
| Tacrolimus | Prostaglandins | Tretinoin | Genistein |
| Everolimus | Abciximab | Halofuginone | Statins |
| Biolimus A9 | | Prolylhydroxylase inhibitors | Tyrosinkinase inhibitors |
| Cyclosporin A | | MMP inhibitors | VEGF |
| Mycophenolic acid | | Batimastat | EPC antibodies |
| Corticosteroids | | | NO donors |
| Diclofenac Sodium salt | | | |
| Paclitaxel | | | |
| Colchicine | | | |
| Methotrexate | | | |
| Actinomycin D | | | |
| Tranilast | | | |
| Mitomycin | | | |
| QP-2 | | | |
| Vincristine | | | |
| Angiopeptin | | | |
| ABT 578 | | | |
| Pimecrolimus | | | |

In addition to strictly medicinal aspects, factors such as the molecular weight and protein-binding capacity of the active ingredients determined to a significant extent the elution behavior of the active ingredients in the implants. The active ingredients described hereinabove having a molecular weight in the range of 100-2000 Dalton are especially preferred. Such active ingredients are preferably released in a controlled manner by the diffusion-controlling layer.

The exemplary embodiments of the active ingredients that may be used according to the present disclosure may be combined with one another in all conceivable variants but also with other preferred embodiments disclosed herein.

Another aspect of the present disclosure is a method for producing an implant.

The materials described for the implant, in particular, for the implant base body, the primer layer, the active ingredient layer and the diffusion-controlling layer, including the respective exemplary embodiments, may also preferably be used for the production process.

The preparation to be used according to the present disclosure for the primer layer usually also comprises one or more solvents in addition to the primer materials to be used. The coating of the surface of the implant base body with the preparation for the primer layer is applied by means of conventional methods, e.g., by physical vapor-phase deposition (preferably for DLC), chemical vapor-phase deposition (preferably for SiC and parylene). For the exemplary embodiment in which the implant base body is an stent base body, as described hereinabove, the primer layer is preferably applied to the abluminal side of the stent base body or parts thereof, i.e., the surface or parts of the surface of the stent base body which come in contact with the human tissue or animal tissue of the vessels or organs. This may preferably be accomplished because the luminal surface of the stent base body, i.e., the surface of the stent base body or at least parts thereof that come in contact with the lumen of a vessel or another internal cavity of the human or animal body is protected, e.g., by placing the stent on a cylinder, a mandrel, a cannula, and the like, so that the luminal surface does not come in contact with the preparation of the primer layer and therefore is not coated with the primer layer.

The active ingredient coating on the surface or parts of the surface of the implant base body, preferably the stent base body, with primer layer is performed by means of conventional methods, for example, dip methods (dip coating), in which the stent base body is placed on a mandrel, spray coating with a single-substance nozzle and/or multi-substance nozzle, rotational atomization and pressure nozzles, sputtering, and the like.

The active ingredients of the active ingredient layer may be applied in the form of an active ingredient melt or as an active ingredient solvent mixture by means of conventional methods. The usual methods for an active ingredient-solvent mixture include dip coating, where the stent base body is placed on a mandrel, spray coating with a single-substance nozzle and/or a multi-substance nozzle, rotary atomization and pressure nozzles, sputtering, and the like.

If there is an active ingredient-solvent mixture, the solvent should be removed by conventional methods before coating with the diffusion-controlling layer, in particular, by drawing or other physical methods. This serves, in particular, to prevent the polymer of the diffusion-controlling layer from being mixed with the active ingredients, and thus the active ingredient molecules of the active ingredient layer would be present in dispersed (homogenous) form in the diffusion-controlling layer.

For accurate dosing of the active ingredients of the active ingredient layer, the active ingredient melt or the active ingredient solution may be applied to the implant base body, preferably the stent base body, by means of conventional pipetting techniques. If the implant base body, preferably the stent base body, has notching in the form of indentations, depressions, and the like, then the preparation containing the active ingredient is preferably dosed into the indentations, in particular, the notches, depressions, and the like by means of a stream of the active ingredient.

The preparation for the diffusion-controlling layer comprises the polymers described hereinabove including the exemplary embodiments as well as one or more solvents.

The coating of the surface or parts of the surface of the implant base body, preferably the stent base body, is likewise usually performed by dip coating where the stent base body is placed on a mandrel, by spray coating with single-substance nozzle and/or multi-substance nozzle, rotary atomization and pressure nozzles, sputtering, and the like.

The solvents in the preparation for the diffusion-controlling layer are preferably selected so that they do not dissolve the active ingredients of the active ingredient layer at least in part. Therefore, there is little or no significant mixing of the diffusion-controlling layer with the dissolved active ingredient compounds.

The coating steps of the primer preparation described hereinabove, the preparation containing the active ingredients and/or the diffusion-controlling preparation may also be treated further independently of one another after the respective coating step by suitable drawing steps or other conventional physical or chemical aftertreatment steps.

FIG. 1 shows a detail of a cross section of a stent 1 of a stent coated according to the present disclosure.

In addition, FIG. 1 shows the primer layer 2 which comes in contact with the surface of the implant base body as well as the active ingredient layer 3. The materials described hereinabove may be used for this purpose and may be applied entirely or partially to the surface of the stent by conventional methods.

In addition, FIG. 1 shows that the active ingredient layer 3 is arranged between the primer layer 2 and the diffusion-controlling layer 4. As described hereinabove, one, two, three, four or more active ingredients may be used. These active ingredients are applied entirely or partially to the surface of the stent base body with primer, in particular, by conventional methods by means of an active ingredient melt or an active ingredient-solvent mixture.

In addition, FIG. 1 shows that the diffusion-controlling layer 4 is arranged on the surface of the active ingredient layer 3. The diffusion-controlling layer is preferably arranged on the entire surface of the active ingredient layer 3. When the active ingredient layer 3 is applied partially to the primer layer 2, in particular, in the form of islands of active ingredient (not shown here), the diffusion-controlling layer 4 is preferably also in contact with the primer layer 2.

The diffusion-controlling layer 4 may comprise diffusion channels 41 which either are already formed during the coating or are formed subsequently under physiological conditions. The diffusion channels are preferably so large that the active ingredients, in particular, with a molecular weight of 100 to 2000 Dalton, may diffuse out of the active ingredient layer 3 through the diffusion-controlling layer 4 into the human or animal body.

Figure 2:
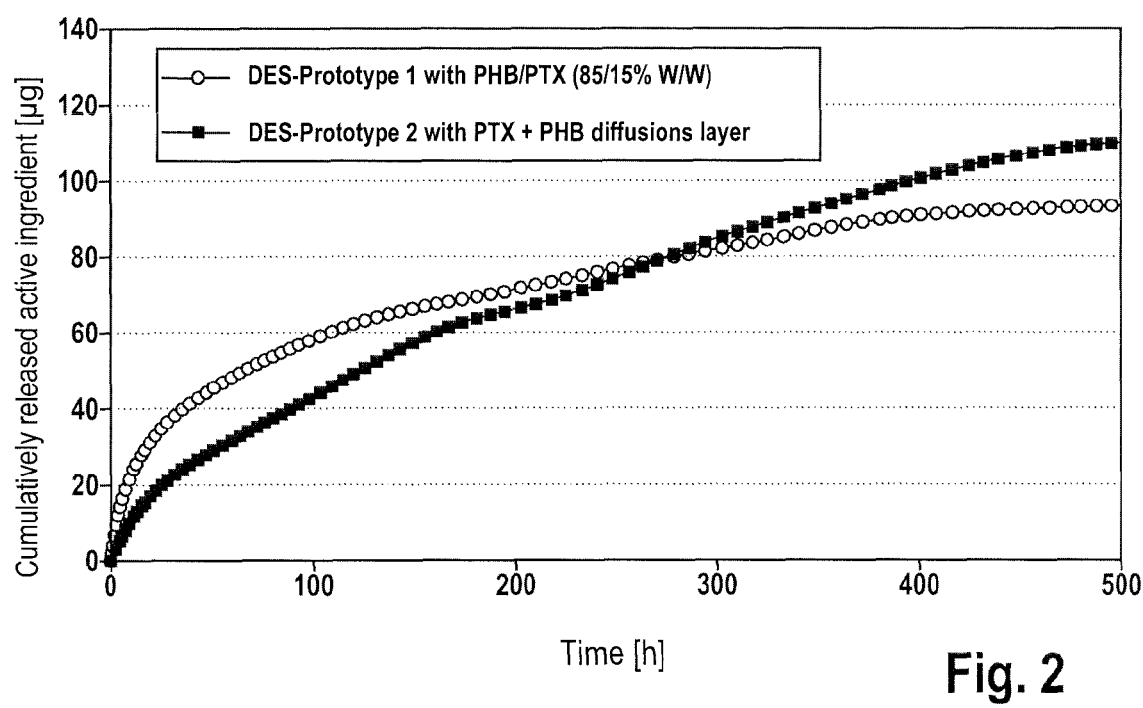
FIG. 2 shows a graphic plot of the in-vitro release of paclitaxel (PTX) from PHB stent coatings.

FIG. 2 shows experimental data of in-vitro release of paclitaxel (PTX) from PHB stent coatings with a different layer structure (each with n=2) in PBS (37° C.); DES prototype 1: PHB coating with incorporation of 15% PTX (approx. 100 µg), DES prototype 2: PTX base layer (approx. 100 µg) with PTX-free PHB top layer (approx. 150 µg).

The exemplary embodiments shown in the figures are also applicable to the description of the present disclosure hereinabove, in particular, its exemplary embodiments.

EXAMPLES

The present disclosure is described hereinbelow through examples, although the examples do not limit the scope of the present invention.

Example 1

CoCr stents with a primer layer (2-10 nm) based on silicon carbide were used. These stents, which were first weighed on an analytical balance, were coated with a 0.1% acetonic paclitaxel (PTX) solution by the spray method. An electropneumatic coating system was used for coating the stents by the spray method. With this system, stent types of a wide variety of dimensions can be coated with polymer solutions and active ingredient solutions in an automated operation. The spray parameters were adjusted so as to yield a uniform PTX distribution on the stent surface. Then by spraying a 0.16% polyhydroxybutyric acid (PHB) solution containing chloroform to the PTX layer, the diffusion-controlling polymeric biodegradable top layer was applied. The stents were then dried for 15 minutes at room temperature and subjected to microscopic visual inspection. After storage of the coated stents for two days in a vacuum drying cabinet (6-8 mbar) at 40° C., the stents were again weighed for a gravimetric determination of the weight of the layer. To determine the layer thicknesses, stent samples embedded in cold-curing epoxy resin were analyzed with the help of light microscopic methods and image analysis methods. The layer thicknesses thereby ascertained amounted to an average of 5 µm for the active ingredient layer and 10 μm for the PHB layer. In this exemplary embodiment, the in-vitro behavior of stents in releasing the active ingredient in phosphate buffer (PBS) at 37° C. is shown in FIG. 2 in comparison with PHB coating with PTX incorporation without an external diffusion-controlling PHB coating.

FIG. 2 shows that on incorporation of the active ingredient paclitaxel in a polymer layer (DES prototype 1) in comparison with the diffusion-controlling coating (DES prototype 2) according to the present disclosure, a bolus-type release of active ingredient was observed which is unwanted, especially with very strong active ingredients such as paclitaxel.

The designs depicted in the description of the exemplary embodiments should also be applied to the description of the invention given above, in particular, the exemplary embodiments thereof.

All patents, patent applications and publications referred to herein are incorporated by reference in their entirety.

What is claimed is:

1. An implant having a structure for implantation in a human or animal body, the implant comprising:
    a) an implant base body;
    b) a primer layer applied at least partially to the surface of the implant;
    c) an active ingredient layer consisting of one or more active ingredients applied to at least a portion of the surface of the primer layer; and
    d) a diffusion-controlling layer applied to at least a portion of the active ingredient layer and a portion of the primer layer, wherein diffusion of the active ingredients of the active ingredient layer is controlled.

2. The implant of claim 1, wherein the primer layer is one or more materials selected from the group consisting of silicon carbide (SiC), diamond-like carbon (DLC), pyrolytic carbon (pyC), a parylene, glycocalix, and hydroxyapatite.

3. The implant of claim 1, wherein the diffusion-controlling layer comprises one or more polymers selected from the group consisting of a polyester, a polyurethane, a silicon, a polyorganophosphazene, a polymethacrylate, a polystyrene block copolymer, a polyethylene-co-vinyl acetate, a polyethylene terephthalate or a blend or a copolymer thereof, and a phosphorylcholine polymer or polysaccharide.

4. The implant of claim 1, wherein the one or more active ingredients of the active ingredient layer are each independently selected from the group consisting of an antiphlogistic, a cytostatic, an immunosuppressant, a platelet aggregation inhibitor, a statin, an estrogen, a lipid regulator, a vasodilator, a calcium channel blocker, a calcineurin inhibitor, an anti-inflammatory drug, an anti-allergic, an oligonucleotide, an endothelium-forming agent, a steroid, a protein, a peptide, a proliferation inhibitor, an analgesic, and an antirheumatic.

5. The implant of claim 1, wherein the implant base body is selected from the group consisting of a heart pacemaker, a brain pacemaker, a heart implant, a pacemaker electrode, a defibrillation electrode, a cochlear implant, an implant for dental medicine, a depot implant that serves to form a depot of an active ingredient, a biodegradable or permanent coronary or peripheral stent, a biodegradable or permanent stent for an internal cavity, and a local drug delivery implant.

6. The implant of claim 1, wherein the implant base body is a permanent or biodegradable coronary stent.

7. A method for manufacturing an implant, the method comprising:
    a) providing an implant having a structure for implantation in a human or animal body, the implant comprising:
        (i) an implant base body;
        (ii) a preparation for a primer layer comprising one or more primer materials;
        (iii) a preparation for an active ingredient layer comprising one or more active ingredients; and
        (iv) a preparation for a diffusion-controlling layer comprising one or more polymers and one or more solvents;
    b) coating at least a portion of the implant base body with the preparation for the primer layer;
    c) coating a portion of the at least partially coated implant base body from step b) with the preparation for the active ingredient layer; and
    d) coating at least a portion of the at least partially coated implant base body from c) with the preparation for the diffusion-controlling layer and a portion of the primer layer.

8. The implant of claim 3, wherein the diffusion controlling layer polymer is one or more materials selected from the group consisting of polydioxanone, polyglycolide, polycaprolactone, polyhydroxyvaleric acid, a polyhydroxybutyric acid, a polylactide, and a copolymer of the foregoing.

9. The implant of claim 3, wherein the diffusion controlling layer polysaccharide is one or more materials selected from the group consisting of chitosan, hyaluronic acid, heparin, dextran and cellulose.

10. The implant of claim 4, wherein the antiphlogitic is selected from the group consisting of dexamethasone, methylprednisolone and diclofenac.

11. The implant of claim 4, wherein the cystostaic is selected from the group consisting of paclitaxel, colchicine, actinomycin D and methotrexate.

12. The implant of claim 4, wherein the immunosuppressant is selected from the group consisting of a limus compound, sirolimus (rapamycin), zotarolimus (ABT-578), tacrolimus (FK-506), everolimus, biolimus, biolimus A9, pimecrolimus, cyclosporin A and mycophenolic acid.

13. The implant of claim 4, wherein the platelet aggregation inhibitor is abciximab or iloprost.

14. The implant of claim 4, wherein the statin is selected from the group consisting of simvastatin, mevastatin, atorvastatin, lovastatin, pitavastatin and fluvastatin.

15. The implant of claim 4, wherein the estrogen is selected from the group consisting of 17β-estradiol, daidzein and genistein.

* * * * *